United States Patent [19]

Li

[11] 4,098,778

[45] Jul. 4, 1978

[54] β-ENDORPHIN ANALOG

[75] Inventor: Choh Hao Li, Berkeley, Calif.

[73] Assignee: Hoffmann-La Roche Inc., Nutley, N.J.

[21] Appl. No.: 811,651

[22] Filed: Jun. 30, 1977

Related U.S. Application Data

[63] Continuation-in-part of Ser. No. 776,568, Mar. 11, 1977, Pat. No. 4,081,434, and a continuation-in-part of Ser. No. 777,262, Mar. 14, 1977.

[51] Int. Cl.$^2$ .................... C07C 103/52; A61K 37/00
[52] U.S. Cl. ............................. 260/112.5 R; 424/177
[58] Field of Search ................. 260/112.5 R; 424/177

[56] References Cited
PUBLICATIONS

Li, et al., Biochem. and Biophys. Res. Commun. 75, 1977, pp. 576–580.
Lazarus, et al., Proc. Nat'l. Acad. Sci USA 73, pp. 2156–2159, 1976.
Ling, et al., Proc. Nat'l. Acad. Sci USA 73, pp. 3308–3310, 1976.
Snyder, et al., Journal of Neurochem. 28, 1977, pp. 13–20.

*Primary Examiner*—Delbert R. Phillips
*Attorney, Agent, or Firm*—Samuel L. Welt; George M. Gould

[57] ABSTRACT

The β-endorphin analog β-endorphin (6–31), although lacking the enkephalin moiety i.e., β-endorphin (1–5) exhibits analgesic activity which is not reversed by naloxone.

4 Claims, No Drawings

β-ENDORPHIN ANALOG

RELATED APPLICATIONS

This application is a continuation-in-part of copending U.S. Patent Applications Ser. No. 776,568, U.S. Pat. No. 4,081,434, Mar. 28, 1978 filed Mar. 11, 1977 and Ser. No. 777,262, pending filed Mar. 14, 1977.

BACKGROUND OF THE INVENTION

Recent studies have shown that β-endorphin from camel and human pituitary glands not only exhibits many of the biological properties associated with similar opiate-like peptides, but exhibits these activities to a substantially greater degree. The structural feature common to this family of peptides is an enkephalin segment corresponding to positions 1–5 of β-endorphin, which constitutes a minimal requirement for elicitation of opiate-like activity. On the other hand, the "non-enkephalin" segment, i.e., residues 6–31, plays an important role in the unique actions of β-endorphin.

DESCRIPTION OF THE INVENTION

The present invention relates to novel analogs of β-endorphin which analogs have the sequence β-endorphin (6–31). These compounds have opiate agonist and analgesic activity which are not reversed by naloxones.

For the purpose of this disclosure the term β-endorphin is intended to emcompass the various sequences which result from species variability. Thus β-endorphin will include, for example, β-endorphin having a sequence derived from human ($β_h$-endorphin), camel ($β_c$-endorphin) or porcine ($β_p$-endorphin) sources.

Thus, in particular, the present invention relates to the following specific compounds:
$β_h$-endorphin (6–31)
$β_c$-endorphin (6–31)
$β_p$-endorphin (6–31)

These compounds exhibit essentially equivalent levels of biological activity.

The compounds of the invention can be conveniently prepared by solid phase synthesis in analogy to the strategy disclosed in U.S. patent application Ser. No. 667,747, filed Mar. 17, 1976 except that the amino acids contained in the residue 1–5 of β-endorphin are not included in the cycles. Any conventional solid phase synthesis resin may be employed in this procedure. A particularly preferred resin is chloromethylated copolystyrene-divinylbenzene resin.

The compounds of the present invention exhibit measurable analgesic activity as assessed in mice by the tail flick method. Thus, for example $β_c$-endorphin-(6–31) at doses of 42.5 and 85 ug produced a slight inhibition of the tail-flick response. Such activity must be considered surprising since this compound does not contain the metenkephalin sequence which heretofore has been considered a critical determinant for opiate-receptor mediated analgesics. The comparative potency of $β_c$-endorphin-(6–31) is 4% of $β_c$-endorphin as assayed in vitro but most critically such activity is not reversed by naloxone. See in this regard Li et al., Biochem. Biophys. Res. Commun. 75, 576 (1977). Thus the compounds of the invention have the potential of being non-addictive analgesic agents.

The β-endorphin analogs of the present invention can be employed as opiate agonists and as analgesic agents in the same manner as their parent compounds with dosage being adjusted for their relative potency.

Sterile, stabile solid dosage forms for reconstitution for parenteral administration are obtained by filtering aqueous buffered solutions of the desired compound of the invention through a sterilizing filter into sterile vials and then lyophilizing. The solid lyophilized product can be reconstituted at the time of use by the addition of sterile, isotonic saline. Other parenteral dosage forms known in the art for the administration of peptides can also be used.

The syntheses and biological properties of the compounds of invention are illustrated in the following Examples.

EXAMPLE 1

Experimental and Results

Thin-layer chromatography (tlc) was run on silica gel in 1-butanol-pyridine-acetic acid-water (5:5:1:4) with detection by ninhydrin and chlorine-tolidine reagents. Paper electrophoresis on Whatman 3 MM was carried out for 4–5 hr at 400 V and 24° in pyridine-acetate, pH 3.7, and in γ-collidine-acetate, pH 6.7. Detection was with ninhydrin and $R_f$ values were measured relative to lysine.

Carboxymethylcellulose chromatography was performed in a 1.23 × 47 cm column at 24° with an initial buffer of 0.01 M NH$_4$OAc of pH 4.5 and collection of 10 ml fractions at about 200 ml/hr. A gradient with respect to pH and salt concentrations was effected by introducing NH$_4$OAc buffers (as subsequently described) through a 500-ml mixing chamber containing the starting buffer.

Partition chromatography on Sephadex G-25 and on Sephadex G-50 was performed by reported procedures such as Yamashiro, Nature (London) 201,76 (1964) or Yamashiro and Li, J.Am.Chem.Soc. 95, 1310 (1973).

Solid-Phase Synthesis Procedures

Boc-Gln-OH and Boc-Glu-(OBzl)-OH were esterified to brominated polystyrene polymer crosslinked with divinylbenzene by the Loffet method, Int. J. Protein Res. 3, 297 (1971) in DMF to give a stable linkage to the polymer. The procedures for attachment of the remaining amino acid residues were those described for the synthesis of human β-endorphin by Li et al., J. Med. Chem. 20, 325 (1977). Side-chain protection for the His residue was Z (benzyloxycarbonyl). For the met-containing peptides, the Boc group of the last amino acid residue was removed with trifluoroacetic acid to reduce the t-butylation that occurs in HF.

Isolation of Peptides

Protected peptide resins were treated with HF in the presence of anisole and the products were subjected to gel filtration on Sephadex G-10 as previously described by Li et al., supra. For chromatography on carboxymethylcellulose the following buffer profiles were used: $β_c$-endorphin-(6–31), 0.2 M NH$_4$OAc after fraction 5, 0.4 M NH$_4$OAc after fraction 26 (product peak in fraction 40).

The product was then purified by partition chromatography as follows: $β_c$-endorphin-(6–31), 1.91 × 29.8 cm Sephadex G-25, 1-butanol-ethanol- 2 M NH$_4$OAc (4:2:5), $R_f$ 0.30. The approximate overall yield was $β_c$-endorphin-(6–31), from 50 μmol starting resin, 48 mg (33%).

The peptide (50 μg sample) was homogeneous in paper electrophoresis at pH 3.7 and pH 6.7 with the following $R_f$ value: $\beta_c$-endorphin-(6-31), 0.72 and 0.52. A satisfactory solvent system for tlc of $\beta_c$-endorphin-(6-31) was not found.

Amino acid analyses, as performed by the procedure of Spackman et al., Anal. Chem. 30, 1190 (1958) were in good agreement with expected values as seen in Table 1 below.

Table 1

Amino Acid Analysis of $\beta$-Endorphin Analogs

| Amino Acid | Acid Hydrolysates[a] $\beta_c$-Endorphin(6-31) | | Enzyme Hydrolysates[b] $\beta_c$-Endorphin(6-31) | |
|---|---|---|---|---|
| | Calcd. | Found | Calcd. | Found |
| Lys | 5 | 5.0 | 5 | 4.7 |
| His | 5 | 1.0 | 1 | 0.9 |
| Asp | 2 | 1.9 | | 0.1 |
| Thr | 3 | 2.8 | | |
| Ser | 2 | 1.8 | | |
| Asn | | | 9 | 9.1 |
| Gln | | | | |
| Glu | 3 | 3.2 | 1 | 1.1 |
| Pro | 1 | 1.0 | 1 | 1.0 |
| Gly | 1 | 1.0 | 1 | 1.3 |
| Ala | 2 | 2.2 | 2 | 2.0 |
| Val | 1 | 1.0 | 1 | 1.1 |
| Met | | | | |
| Ile | 2 | 1.3[c] | 2 | 1.8 |
| Leu | 2 | 1.9 | 2 | 2.1 |
| Tyr | | | | |
| Phe | 1 | 0.9 | 1 | 1.1 |

[a]Hydrolysis a constant boiling HCl for 24 hr.
[b]Treatment with trypsin and chymotrypsin followed by leucine aminopeptidase.
[c]Low values accounted for by Ile-Ile moiety.

EXAMPLE 2

Biological Activity

The analgesic activity of the synthetic products was assessed in mice by the tail-flick method of D'Amour and Smith J. Pharmacol. Exp. Ther. 72, 74 (1941). Male ICR mice weighing 25–30 g were used. The peptide was injected icv in a volume of 5 $\mu$l as described by Haley and McCormick, Br. J. Pharmacol. 12, 12 (1957). To evaluate the tail-flick response, a control latency ($T_0$) was obtained from the mean of two latencies determined prior to the peptide injection; the test latencies ($T_1$) were determined at various times after injection for each animal. "Percent analgesia" was calculated as $[(T_1-T_0)/(T_2-T_0)] \times 100$; where the cutoff time ($T_2$) was 10 sec. With a twofold increase in latency of reaction time of the reponse as a quantal index of inhibition, the median antinociceptive dose ($AD_{50}$) and 95% confidence limits were calculated as described by Litchfield and Wilcoxon, J. Pharmacol. Exp. Ther. 96, 99 (1949).

$\beta_c$-endorphin-(6-31) at doses of 42.5 and 85 $\mu$g produced a slight inhibition of the tail-flick response which is not as potent as the parent endorphin or other fragment analogs thereof which contain the met-enkephalin sequence. Interestingly, $\beta_c$-endorphin-(6-31) does not contain the met-enkephalin sequence, yet it posseses an intrinsic measurable analgesic activity. It may be noted that $\beta_c$-endorphin-(6-31) possesses 4% potency of $\beta_c$-endorphin as assayed in vitro but its activity is not reversed by naloxone.

The opiate activity of the peptide of the invention, the parent peptide and other fragment analogs thereof as assayed in vitro by the guinea pig ileum method of Kosterlitz et al., Brit. J. Pharmacol. 39, 398 (1970) is seen in Table 2 below.

Table 2

Morphine-like Activity of Synthetic $\beta$-Endorphin Analogs

| Synthetic Peptides | In vitro opiate activity | In vivo analgesic activity | |
|---|---|---|---|
| | | $AD_{50}$[a] | Relative[b] Potency |
| $\beta_c$-Endorphin | 100 | 0.11 (0.07–0.17) | 100 |
| $\beta_c$-Endorphin-(6-31) | 4 | >86 | <0.1 |
| $\beta_h$-Endorphin-(1-5)-(16-31) | 135 | 25.1(16.8–37.1) | 0.3 |
| $\beta_c$-Endorphin-(1-5)-(28-31) | 35 | >86 | <0.1 |

[a]$AD_{50}$ in $\mu$g/mouse (95% confidence limit): 7–10 mice for each dose tested.
[b]Molar basis

EXAMPLE 3

$\beta_h$-Endorphin (6-31)

The procedure of Example 1 is repeated with the exception that the carboxyl terminus group utilized is Boc-Glu(OBzl)-OH and Boc-His(Boc)-OH is replaced by Boc-Tyr(oBr-Z)-OH to thereby produce $\beta_h$-endorphin (6-31).

EXAMPLE 4

$\beta_p$-Endorphin (6-31)

The procedure of Example 1 is repeated with the exception that the first Boc-Ile-OH amino acid is substituted with Boc-Val-OH so as to thereby produce $\beta_p$-endorphin (6-31).

I claim:

1. An analog of $\beta$-endorphin of the sequence $\beta$-endorphin (6-31).
2. The analog of claim 1 which is $\beta_h$-endorphin (6-31).
3. The analog of claim 1 which is $\beta_c$-endorphin (6-31).
4. The analog of claim 1 which is $\beta_p$-endorphin (6-31).

* * * * *